(12) United States Patent
Bell et al.

(10) Patent No.: US 8,592,191 B2
(45) Date of Patent: Nov. 26, 2013

(54) PROCESS FOR FERMENTATION OF SYNGAS

(75) Inventors: Peter Simpson Bell, Fayetteville, AR (US); Ching-Whan Ko, Fayetteville, AR (US)

(73) Assignee: INEOS Bio SA, Lisle, IL (US)

( * ) Notice: Subject to any disclaimer, the term of this patent is extended or adjusted under 35 U.S.C. 154(b) by 0 days.

(21) Appl. No.: 13/473,167

(22) Filed: May 16, 2012

(65) Prior Publication Data

US 2013/0005021 A1  Jan. 3, 2013

Related U.S. Application Data

(60) Provisional application No. 61/571,564, filed on Jun. 30, 2011, provisional application No. 61/571,565, filed on Jun. 30, 2011, provisional application No. 61/573,845, filed on Sep. 13, 2011.

(51) Int. Cl.
 C12P 7/06 (2006.01)
 C12P 7/54 (2006.01)
 C12N 1/20 (2006.01)

(52) U.S. Cl.
 USPC .................. 435/161; 435/140; 435/252.7

(58) Field of Classification Search
 USPC .......................... 435/161, 140, 252.7
 See application file for complete search history.

(56) References Cited

U.S. PATENT DOCUMENTS

| | | | |
|---|---|---|---|
| 5,173,429 A | 12/1992 | Gaddy | |
| 5,593,886 A | 1/1997 | Gaddy | |
| 5,807,722 A | 9/1998 | Gaddy | |
| 5,972,661 A | 10/1999 | Kubera | |
| 6,136,577 A | 10/2000 | Gaddy | |
| 6,368,819 B1 | 4/2002 | Gaddy | |
| 6,500,651 B1 | 12/2002 | Seress | |
| 6,753,170 B2 | 6/2004 | Gaddy | |
| 7,201,884 B2 | 4/2007 | Cohen | |
| 7,285,402 B2 | 10/2007 | Gaddy | |
| 2001/0055237 A1 | 12/2001 | Kubera | |
| 2007/0275447 A1 | 11/2007 | Lewis | |
| 2010/0227377 A1 | 9/2010 | Adams | |
| 2010/0317077 A1 | 12/2010 | Gaddy | |
| 2013/0005010 A1 | 1/2013 | Bell | |
| 2013/0005014 A1 | 1/2013 | Bell | |

FOREIGN PATENT DOCUMENTS

| | | |
|---|---|---|
| WO | WO 98/00558 | 1/1998 |
| WO | WO 00/68407 | 11/2000 |
| WO | WO 01/55237 | 12/2001 |
| WO | WO 02/08438 | 1/2002 |

(Continued)

OTHER PUBLICATIONS

Fermentation and Enzyme Technology, Wang et al., eds., John Wiley and Sons, Inc., New York, 1979, pp. 58,67,72,73,194-197.*

(Continued)

*Primary Examiner* — Rosanne Kosson
*Assistant Examiner* — Larry Moore
(74) *Attorney, Agent, or Firm* — James P. Krueger; INEOS Bio SA

(57) ABSTRACT

A process for fermenting syngas is provided which is effective for decreasing an amount of time needed to inoculate a main reactor. The process includes propagating a culture of acetogenic bacteria to provide an inoculum for a main reactor and fermenting syngas in the main reactor.

8 Claims, 1 Drawing Sheet

(56) References Cited

FOREIGN PATENT DOCUMENTS

| | | |
|---|---|---|
| WO | WO 2007/117157 | 10/2007 |
| WO | WO 2009/022925 | 2/2009 |
| WO | WO 2009/023364 | 2/2009 |
| WO | WO 2009/064200 | 5/2009 |
| WO | WO 2009/112334 | 9/2009 |
| WO | WO 2009/113878 | 9/2009 |
| WO | WO 2009/154788 | 12/2009 |
| WO | WO 2010/227377 | 9/2010 |

OTHER PUBLICATIONS

Kundiyana, et al. "Syngas fermentation in a 100-L pilot scale fermentor: Design and process considerations," J Bioscience and Bioengineering 109(5):492-498, 2010.*

NETL Test Protocol, Testing of Hydrogen Separation Membranes, DOE/NETL-2008/1335, pp. 10-11, http://www.netl.doe.gov/technologies/hydrogen_clean_fuels/refshelf/pubs/Membrane%20test%20protocol%20v10_2008_final10092008.pdf, 2008.*

Bredwell, et al. "Mass-Transfer Properties of Microbubbles", Biotechnol l. Experimental Studies, vol. 14, No. 1,6 Biotechnology Progress, Feb. 1998 pp. 31-38.

Cobb et al. "Production of Synthesis Gas by Biomass Gasification", Proceedings of the 2007 Spring National AIChE Meeting, Houston, Tx, Apr. 22, 2007.

Houben et al., "Tar Reduction Through Partial Combustion of Fuel Gas", Science Direct, Fuel 84(2005): 817-824.

Vander Der Hoeven et al., "Analysis of Hydrogen Influence on Tar Removal by Partial Oxidation", Science Direct, Fuel 85(2006);1.

Skidmore, "Syngas Fermentation Quantificatin of Assay Techniques, Reaction Kinetics, and Pressure Dependencies of the Clostridial P11 Hydrogenase," Thesis, Brigham Young Univ, Apr. 2010.

Kundiyana et al., "Syngas Fermentation in a 100-L Pilot Scale Fermentor: Design and Process Considerations," Journal Bioscience Bioengineering, vol. 109, #5, 492-8, 2010.

Datar, "Fermentation of Biomass Generated Producer Gas to Ethanol," Wiley InerScience, Apr. 15, 2004.

Ungerman et al., "Carbon Monoxode Mass Transfer for Syngas Fermentation in Stirred Tank Reactor with Dual Impeller Configurations," Biotechnol, Prog. 2007, 23, 613-20.

Ismail et al., "Biological Hydrogen Production from CO: Bioreactor Performance," Biochemical Engineering Journal 39 (2008) 468-477.

Sioni, "Microbial Cell Factories, High Cell Density Media for *Escherichia coli* are generally Designed for Aerobic Cultivations-Consequences . . . ", BioMed Central, Aug. 7, 2008.

Mohammdi et al., "Bioconversion of Synthesis Gas to Second Generation Biofuels: A reivew;" Renewable and Sustainable Energy Reviews 15 (2011) 4255-4273.

International Searching Authority PCT/US2012/040322 Search Report and Written Opinion; Dec. 10, 2012.

International Searching Authority PCT/US2012/040327 Search Report and Written Opinion; Sep. 7, 2012.

International Searching Authority PCT/US2012/040319 Search Report and Written Opinion, Jan. 14, 2013.

* cited by examiner

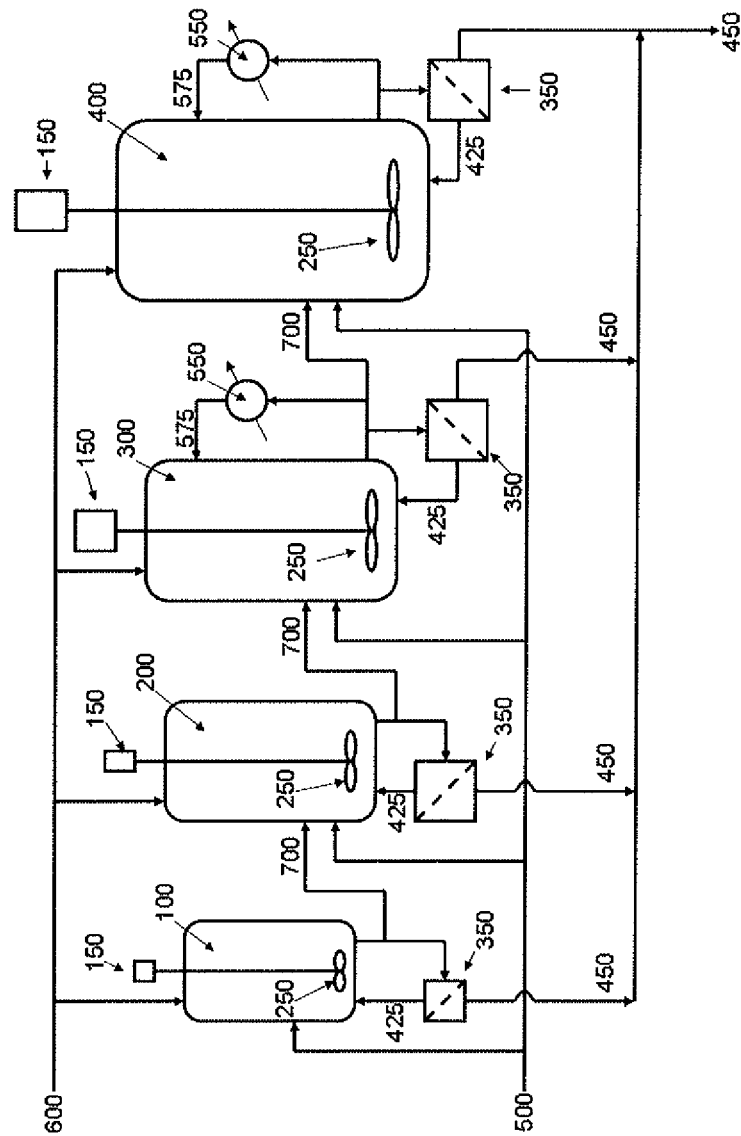

PROCESS FOR FERMENTATION OF SYNGAS

This application claims the benefit of U.S. Provisional Application Nos. 61/571,564 and 61/571,565, both filed Jun. 30, 2011 and 61/573,845, filed Sep. 13, 2011, all of which are incorporated in their entirety herein by reference.

A process is provided for fermentation of syngas. More specifically, the process includes propagating a culture effective for use as an inoculum for a main reactor and fermenting syngas in the main reactor.

BACKGROUND

Anaerobic microorganisms can produce ethanol from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

The CO is often provided to the fermentation as part of a gaseous substrate in the form of a syngas. Gasification of carbonaceous materials to produce producer gas or synthesis gas or syngas that includes carbon monoxide and hydrogen is well known in the art. Typically, such a gasification process involves a partial oxidation or starved-air oxidation of carbonaceous material in which a sub-stoichiometric amount of oxygen is supplied to the gasification process to promote production of carbon monoxide as described in WO 2009/154788.

Fermentation processes with acetogenic bacteria may include one or more seed reactors, one or more growth reactors and at least one main reactor. Acetogenic bacteria are normally grown to a certain cell density in a seed reactor. The seed reactor is then used to inoculate a growth fermentor. The growth fermentor will usually be of a larger size than seed reactor. Acetogenic bacteria in the growth reactor are then grown to a desired cell density. The growth reactor may then be used to inoculate another larger growth reactor or may be used to inoculate a main reactor. The main reactor will be of a larger size than the growth reactor. In view of this process, inoculating a main reactor starting from a seed reactor requires time. Further, if a growth reactor fails, the process needs to be restarted, requiring even more time.

SUMMARY

A process for fermenting syngas is provided which is effective for decreasing an amount of time needed to inoculate a main reactor. In this aspect, the total time from inoculation of a seed reactor to inoculation of a main reactor is decreased. The process also provides for faster restarts in the event of reactor failure.

In one aspect, a process for fermenting syngas is provided that includes propagating a culture of acetogenic bacteria effective for inoculating a main reactor. The propagation includes: i) inoculating a first culture of acetogenic bacteria into a pre-reactor to provide a minimum viable cell density, and ii) growing the culture of acetogenic bacteria in the pre-reactor to provide a pre-reactor target cell density. Propagation may be further described by the following equations: (a) wherein, if (the pre-reactor target cell density multiplied by the pre-reactor volume)÷(a volume of the main reactor multiplied by (a volume of the pre-reactor÷a volume of the pre-reactor which is transferred)) is greater than or equal to a minimum viable cell density, transfer a volume of the pre-reactor to the main reactor in an amount effective for providing a minimum viable cell density in the main reactor, or (b) if (the pre-reactor target cell density multiplied by the pre-reactor volume)÷(a volume of the main reactor multiplied by (a volume of the pre-reactor÷a volume of the pre-reactor which is transferred)) is less than a minimum viable cell density, transfer a volume of the pre-reactor to a subsequent pre-reactor in an amount effective for providing a minimum viable cell density in the subsequent pre-reactor. Step ii is repeated until a volume of pre-reactor is transferred to the main reactor. Fermentation of syngas is then conducted in the main reactor.

In one aspect, a process for fermenting syngas is provided that includes propagating a culture of acetogenic bacteria effective for inoculating a main reactor. The propagation includes: i) inoculating a first culture of acetogenic bacteria into a pre-reactor to provide a minimum viable cell density, and ii) growing the culture of acetogenic bacteria in the pre-reactor to provide a pre-reactor target cell density. Propagation may be further described by the following equations: (a) wherein, if (the pre-reactor target cell density multiplied by the pre-reactor volume)÷(a volume of the main reactor multiplied by (a volume of the pre-reactor÷a volume of the pre-reactor which is transferred)) is greater than or equal to a minimum viable cell density, transfer a volume of the pre-reactor to the main reactor in an amount effective for providing a minimum viable cell density in the main reactor, or (b) if (the pre-reactor target cell density multiplied by the pre-reactor volume)÷(a volume of the main reactor multiplied by (a volume of the pre-reactor÷a volume of the pre-reactor which is transferred)) is less than a minimum viable cell density, adjusting the volume of the main reactor and transferring a volume of the pre-reactor to the main reactor in an amount effective for providing a minimum viable cell density in the main reactor, and increasing the volume of the main reactor while maintaining a minimum viable cell density. Fermentation of syngas is then conducted in the main reactor.

In another aspect, a process is provided for starting a main fermentor for fermentation of syngas. The process includes inoculating a first culture of acetogenic bacteria into a seed reactor to provide a minimum initial viable cell density in the seed reactor of at least about 0.2 grams per liter. The culture of acetogenic bacteria is grown with syngas to provide a cell density in the seed reactor of at least about 5 grams per liter. A first growth reactor is inoculated with an inoculum from the seed reactor in an amount effective for providing a cell density in the growth reactor of at least about 0.2 grams per liter. The culture is grown with syngas to provide a cell density in the first growth reactor of at least about 5 grams per liter. A second growth reactor is inoculated with an inoculum from the first growth reactor in an amount effective for providing a cell density in the growth reactor of at least about 0.2 grams per liter. The culture is grown with syngas to provide a cell density in the second growth reactor of at least about 5 grams per liter. A main fermentor is inoculated with an inoculum from the second growth reactor in an amount effective for providing a cell density in the main reactor of at least about 0.2 grams per liter.

BRIEF DESCRIPTION OF FIGURES

The above and other aspects, features and advantages of several aspects of the process will be more apparent from the following FIGURE.

FIG. 1 illustrates a process for fermenting syngas.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various aspects of the present process and apparatus. Also, common but well-understood elements that are useful or necessary in commercially feasible aspects are often not depicted in order to facilitate a less obstructed view of these various aspects.

DETAILED DESCRIPTION

The following description is not to be taken in a limiting sense, but is made merely for the purpose of describing the general principles of exemplary embodiments. The scope of the invention should be determined with reference to the claims.

A series of one or more pre-reactors is provided which are effective for quickly providing an inoculum to a main reactor. The one or more pre-reactors and main reactor are operatively connected to allow transfer of culture. Each of the one or more pre-reactors is inoculated with a minimal viable cell density and is then grown to provide a target cell density for subsequent inoculation. A volume of about 25% to about 75% of any pre-reactor is transferred to a subsequent reactor. The remaining volume is maintained and can be used for re-inoculation should any subsequent reactor fail.

DEFINITIONS

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

"Carbonaceous material" as used herein refers to carbon rich material such as coal, and petrochemicals. However, in this specification, carbonaceous material includes any carbon material whether in solid, liquid, gas, or plasma state. Among the numerous items that can be considered carbonaceous material, the present disclosure contemplates: carbonaceous material, carbonaceous liquid product, carbonaceous industrial liquid recycle, carbonaceous municipal solid waste (MSW or msw), carbonaceous urban waste, carbonaceous agricultural material, carbonaceous forestry material, carbonaceous wood waste, carbonaceous construction material, carbonaceous vegetative material, carbonaceous industrial waste, carbonaceous fermentation waste, carbonaceous petrochemical co products, carbonaceous alcohol production co-products, carbonaceous coal, tires, plastics, waste plastic, coke oven tar, fibersoft, lignin, black liquor, polymers, waste polymers, polyethylene terephthalate (PETA), polystyrene (PS), sewage sludge, animal waste, crop residues, energy crops, forest processing residues, wood processing residues, livestock wastes, poultry wastes, food processing residues, fermentative process wastes, ethanol co-products, spent grain, spent microorganisms, or their combinations.

The term "fibersoft" or "Fibersoft" or "fibrosoft" or "fibrousoft" means a type of carbonaceous material that is produced as a result of softening and concentration of various substances; in an example carbonaceous material is produced via steam autoclaving of various substances. In another example, the fibersoft can include steam autoclaving of municipal, industrial, commercial, and medical waste resulting in a fibrous mushy material.

The term "municipal solid waste" or "MSW" or "msw" means waste that may include household, commercial, industrial and/or residual waste.

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas comprises use as an intermediate in producing synthetic petroleum for use as a fuel or lubricant via Fischer-Tropsch synthesis and previously the Mobil methanol to gasoline process. Syngas consists primarily of hydrogen, carbon monoxide, and some carbon dioxide, and has less than half the energy density (i.e., BTU content) of natural gas. Syngas is combustible and is often used as a fuel source or as an intermediate for the production of other chemicals.

The terms "fermentation", fermentation process" or "fermentation reaction" and the like are intended to encompass both the growth phase and product biosynthesis phase of the process. In one aspect, fermentation refers to conversion of CO to alcohol.

Pre-Reactor Design

In accordance with the process, a culture of acetogenic bacteria is inoculated into a pre-reactor to provide a minimum cell density. In this aspect, the pre-reactor may be one or more seed reactors and one or more growth reactors. The seed reactor may have a volume of about 500 liters or less, in another aspect, about 400 liters or less, in another aspect, about 300 liters or less, in another aspect, about 200 liters or less, in another aspect, about 100 liters or less, and in another aspect, about 50 liters or less. Growth reactors may have a volume of about 250,000 liters or less, in another aspect, about 150,000 liters or less, in another aspect, about 100,000 liters or less, in another aspect, about 50,000 liters or less, in another aspect, about 10,000 liters or less, and in another aspect, about 1,000 liters or less. As used herein, "volume" refers to a non-gassed liquid working volume.

The seed reactor may be supplied with syngas, including for example bottled syngas. In this aspect, using a seed reactor having a volume of 500 liters or less allows the seed reactor to be supplied with bottled syngas. The use of bottled syngas may be important if a supply of syngas from a gasification process is not available. Useful syngas compositions are described herein. In one aspect, pre-reactors may be supplied with gas recycled from the main reactor.

Culture in the seed reactor is grown to a pre-reactor target cell density and a volume of the seed reactor is used to inoculate a subsequent pre-reactor having a larger volume than the seed reactor. In this aspect, the second pre-reactor may be one or more growth reactors. In an important aspect, the process utilized at least two growth reactors, in another aspect, at least three growth reactors, and in another aspect at least four growth reactors.

One aspect of a process for fermenting syngas is generally illustrated in FIG. 1. In this aspect, the process includes a seed reactor 100, a first growth reactor 200, a second growth reactor 300, and a main reactor 400. Each reactor can be supplied with syngas through a gas supply 500. Nutrients may be supplied to each reactor through nutrient supply 600. Each reactor may include an agitator 150 and at least one impeller 250. Medium from each reactor may be sent to a cooler/heat exchanger 550 and cooled medium may be cycled back to the reactor vessel. Medium from one reactor may be transferred to the next reactor through a transfer line 700.

Medium from each reactor may be sent to a recycle filter 350. Concentrated cells 425 may be returned to the reactor vessel and permeate 450 may be sent for further processing. Further processing may include separation of desired product such as for example ethanol, acetic acid and butanol.

Pre-Reactor Operation

Pre-reactor operation allows for a rapid start up for a main reactor inoculation. In this aspect, the time from inoculation of a first pre-reactor to inoculation of a main reactor is about 20 days or less, in another aspect, about 15 days or less, and in another aspect, about 10 days or less. The process also allows for a more rapid recovery should any of the pre-reactors fail.

In accordance with the process, a culture of acetogenic bacteria is inoculated into a pre-reactor or seed reactor to provide a minimum cell density. As used herein, "minimum cell density" means a viable cell density of at least about 0.1 grams per liter, in another aspect, at least about 0.2 grams per liter, in another aspect, at least about 0.3 grams per liter, in another aspect, at least about 0.4 grams per liter, and in another aspect, at least about 0.5 grams per liter. The minimum cell density will not exceed about 1.2 grams per liter. In another aspect, the first culture used to inoculate a pre-reactor or seed reactor has a pH of 6.5 or less, in another aspect 4.5 or less, and in another aspect, about 4.0 to about 4.5. The first culture used to inoculate a pre-reactor or seed reactor has an acetic acid concentration of about 10 grams per liter or less, in another aspect, about 1 to about 10 grams per liter, in another aspect, about 1 to about 5 grams per liter, in another aspect, about 1 to about 3 grams per liter, and in another aspect, about 2 grams per liter.

The acetogenic bacteria is grown in the pre-reactor until a target cell density is reached. As used herein, "pre-reactor target cell density" means a viable cell density of at least about 5 grams per liter, in another aspect, at least about 10 grams per liter, in another aspect, at least about 15 grams per liter, and in another aspect, at least about 20 grams per liter. The pre-reactor target cell density will generally not exceed about 50 grams per liter. In another aspect, the pre-reactor target cell density is about 12 to about 15 grams per liter, and in another aspect, about 20 to about 24 grams per liter.

In one aspect, each subsequent pre-reactor has a larger volume than its preceding pre-reactor. In accordance with this process, a volume ratio of the pre-reactor volume transferred to a subsequent pre-reactor or main reactor is about 0.02 to about 0.5, and in another aspect, about 0.02 to about 0.2. In another aspect, about 20 to about 75% of a volume of a pre-reactor is used to inoculate a subsequent pre-reactor or main reactor. Other reactor volumes that may be transferred include about 30 to about 70%, about 40 to about 60%, and about 45 to about 55%. In this aspect, maintaining a volume allows for faster recovery should a subsequent reactor fail. As used herein, "reactor failure" refers to a condition where no gas conversions are taking place and cells appear visually dead after microscopic evaluation. In this aspect, once a reactor failure occurs, the reactor may be re-inoculated within 24 hours.

Upon reaching a target cell density in a pre-reactor, subsequent steps in the process may be described as follows:

$$\text{if } \frac{(\text{pre-reactor target cell density}) \times (\text{pre-reactor volume})}{(\text{volume of main reactor}) \times \left[\frac{(\text{volume of pre-reactor})}{(\text{volume of pre-reactor transferred})}\right]} \geq \text{minimum viable cell density}$$

then a volume of the pre-reactor is transferred to a main reactor in an amount effective for providing a minimum cell density in the main reactor; or $$\text{if } \frac{(\text{pre-reactor target cell density}) \times (\text{pre-reactor volume})}{(\text{volume of main reactor}) \times \left[\frac{(\text{volume of pre-ractor})}{(\text{volume of pre-reactor tranferred})}\right]} \leq \text{minimum viable cell density}$$

then a volume of the pre-reactor is transferred to a subsequent pre-reactor in an amount effective for providing a minimum cell density in the main reactor. This step of transferring from one pre-reactor to another may be repeated until transfer to a main reactor.

In another aspect, upon reaching a target cell density in a pre-reactor, subsequent steps in the process may be described as follows:

$$\text{if } \frac{(\text{pre-reactor target cell density}) \times (\text{pre-reactor volume})}{(\text{volume of main reactor}) \times \left[\frac{(\text{volume of pre-reactor})}{(\text{volume of pre-reactor transferred})}\right]} \geq \text{minimum viable cell density}$$

then a volume of the pre-reactor is transferred to a main reactor in an amount effective for providing a minimum cell density in the main reactor; or $$\text{if } \frac{(\text{pre-reactor target cell density}) \times (\text{pre-reactor volume})}{(\text{volume of main reactor}) \times \left[\frac{(\text{volume of pre-reactor})}{(\text{volume of pre-reactor transferred})}\right]} \leq \text{minimum viable cell density}$$

then a volume of the main reactor may be adjusted and a volume of the pre-reactor may be transferred in an amount to provide a minimum viable cell density in the main reactor. The volume of the main reactor is then increased over time to a desired volume while maintaining a minimum viable cell density.

Each reactor may be operated in a manner effective for maximizing cell growth and maintaining culture health. In one aspect, medium used in each reactor may be the same or different. Examples of suitable mediums include those described in U.S. Pat. No. 7,285,402, PCT/US2009/001522, and U.S. Provisional Application Nos. 61/458,899, 61/458,903, and 61/458,976, all filed Dec. 3, 2010, and all of which are incorporated in their entirety herein by reference. Higher concentration levels of one or more vitamins may be used during growth phase.

In one aspect, a seed reactor may be inoculated with about 0.3 to about 0.7 grams of cells per liter. Syngas may be sparged into the seed reactor at a rate of about 0.5 to about 2.0 liters per minute, in another aspect, about 0.75 to about 1.25 liters per minute. Initial agitation is conducted at about 10 to about 40% of full agitation power. Agitation rates may be increased up to full power over an hour. For example, agitation rates may be increased from about 100 to about 1000 rpm for smaller reactors, and the increases may be correspondingly less for larger reactors.

Acetogenic Bacteria

In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui*, *Acetoanaerobium noterae*, *Acetobacterium woodii*, *Alkalibaculum bacchi* CP11 (ATCC BAA-1772), *Blautia producta*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei*, *Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), *Clostridium magnum*, *Clostridium pasteurianum* (DSM 525 of DSMZ Germany), *Clostridium ragsdali* P11 (ATCC BAA-622), *Clostridium scatologenes*, *Clostridium thermoaceticum*, *Clostridium ultunense*, *Desulfotomaculum kuznetsovii*, *Eubacterium limosum*, *Geobacter sulfurreducens*, *Methanosarcina acetivorans*, *Methanosarcina barkeri*, *Morrella thermoacetica*, *Morrella thermoautotrophica*, *Oxobacter pfennigii*, *Peptostreptococcus productus*, *Ruminococcus productus*, *Thermoanaerobacter kivui*, and mixtures thereof.

Syngas

Syngas may be provided from any know source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. The syngas will have a $CO/CO_2$ molar ratio of at least about 0.75. Some examples of suitable gasification methods and apparatus are provided in U.S. Ser. Nos. 61/516,667, 61/516,704 and 61/516,646, all of which were filed on Apr. 6, 2011, and all of which are incorporated herein by reference.

In another aspect, syngas utilized for propagating acetogenic bacteria may be substantially CO. As used herein, "substantially CO" means at least about 50 mole % CO, in another aspect, at least about 60 mole % CO, in another aspect, at least about 70 mole % CO, in another aspect, at least about 80 mole % CO, and in another aspect, at least about 90 mole % CO.

EXAMPLE

Example 1

Start-Up with Two Growth Reactors

A seed fermentor (90 liters) is inoculated with *Clostridium ljungdahlii*. Syngas was fermented until a cell density of about 12 grams/liter is obtained. Half of the seed fermentor (about 45 liters) is used to inoculate a first growth reactor to provide a total volume in the first growth reactor of about 1390 liters and a starting cell density of about 0.38 grams per liter. Syngas is fermented for 140 hours from time of inoculation to provide a cell density of about 12 grams per liter. Culture from the first growth reactor (about 703 liters) is used to inoculate a second growth reactor to provide a total volume in the second growth reactor of about 22200 liters and a cell density of about 0.38 grams per liter. Syngas is fermented for 140 hours from time of inoculation to provide a cell density of about 12 grams per liter. Culture from the second growth reactor (about 12,000 liters) is used to inoculate a main reactor to provide a total volume in the main reactor of about 350,000 to 400,000 liters and a cell density of about 0.40 grams per liter. The total elapsed time from inoculation of the first growth reactor to inoculation of the main reactor is 11.7 days.

Example 2

Start-Up with Seed Reactor and One Growth Reactors

A seed fermentor (about 1600 liters) is inoculated with *Clostridium ljungdahlii*. Syngas was fermented until a cell density of about 12 grams/liter is obtained. Half of the seed fermentor (about 700 liters) is used to inoculate a first growth reactor to provide a total volume in the first growth reactor of about 2250 liters and a starting cell density of about 0.38 grams per liter. Syngas is fermented for 140 hours from time of inoculation to provide a cell density of about 12 grams per liter. Culture from the first growth reactor (about 11,000 liters) is used to inoculate a main reactor to provide a total volume in the main reactor of about 350,000 to about 400,000 liters and a cell density of about 0.38 grams per liter. The total elapsed time from inoculation of the first growth reactor to inoculation of the main reactor is 9.2 days.

While the invention herein disclosed has been described by means of specific embodiments, examples and applications thereof, numerous modifications and variations could be made thereto by those skilled in the art without departing from the scope of the invention set forth in the claims.

What is claimed is:

1. A process for fermenting syngas comprising propagating a culture of acetogenic bacteria effective for inoculating a main reactor, the propagating including, i) inoculating a first culture of acetogenic bacteria into a pre-reactor to provide a minimum viable cell density of at least 0.2 grams per liter, ii) growing the culture of acetogenic bacteria in the pre-reactor to provide a pre-reactor target cell density of at least 5 grams per liter, (a) wherein, if (the pre-reactor target cell density multiplied by the pre-reactor volume)/(a volume of the main reactor multiplied by (a volume of the pre-reactor/a volume of the pre-reactor which is transferred)) is greater than or equal to a minimum viable cell density, transfer a volume of the pre-reactor to the main reactor in an amount effective for providing a minimum viable cell density in the main reactor, or (b) if (the pre-reactor target cell density multiplied by the pre-reactor volume)/(a volume of the main reactor multiplied by (a volume of the pre-reactor/a volume of the pre-reactor which is transferred)) is less than a minimum viable cell density, transfer a volume of the pre-reactor to a subsequent pre-reactor in an amount effective for providing a minimum viable cell density in a subsequent pre-reactor, and iii) repeat step ii until a volume of pre-reactor is transferred to the main reactor.

2. The process of claim 1 wherein about 25% to about 75% of a volume of a pre-reactor is used to inoculate a subsequent pre-reactor or main reactor.

3. The process of claim 1 wherein a volume ratio of the pre-reactor volume transferred to a subsequent pre-reactor volume or main reactor volume is about 0.02 to about 0.5.

4. The process of claim 1 wherein the syngas has a $CO/CO_2$ molar ratio of at least 0.75.

5. The process of claim 1 wherein the first culture has a pH of 6.5 or less and an acetic acid concentration of 10 grams per liter or less.

6. The process of claim 1 wherein the syngas has about 20 to about 100 mole % CO.

7. The process of claim 1 wherein the syngas used for propagating acetogenic bacteria is substantially CO.

8. The process of claim 1 wherein the acetogenic bacteria is are selected from the group consisting of *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ (Deutsche Sammlung von Mikroorganismen and Zellkulturen) Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* PII (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacefica, Morrella thermoautotrophica, Oxobacter pfennigii, Peptostreptococcus productus, Ruminococcus productus, Thermoanaerobacter kivui*, and mixtures thereof.

* * * * *